US012579737B2

(12) United States Patent
Preston et al.

(10) Patent No.: US 12,579,737 B2
(45) Date of Patent: Mar. 17, 2026

(54) ROTATING 3D SCANNER TO ENABLE PRONE CONTACTLESS REGISTRATION

(71) Applicant: Medtronic Navigation, Inc., Louisville, CO (US)

(72) Inventors: Samantha Joanne Preston, Denver, CO (US); Yvan R. Paitel, Louisville, CO (US); Ryan D. Datteri, Denver, CO (US); Andrew James Summers, Denver, CO (US); Rhythm Agarwal, Boulder, CO (US); Roger Carter, Boulder, CO (US); Hannah Walsh, Denver, CO (US); Abhinaya Ramadugu, Boulder, CO (US); Maitreyee Ramesh Rao, Boulder, CO (US); Wei-Ting Chien, Louisville, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 389 days.

(21) Appl. No.: 17/649,734

(22) Filed: Feb. 2, 2022

(65) Prior Publication Data

US 2023/0245383 A1 Aug. 3, 2023

(51) Int. Cl.
| | |
|---|---|
| *G06T 17/00* | (2006.01) |
| *A61B 34/10* | (2016.01) |
| *A61B 34/20* | (2016.01) |

(52) U.S. Cl.
CPC .............. *G06T 17/00* (2013.01); *A61B 34/10* (2016.02); *A61B 34/20* (2016.02);
(Continued)

(58) Field of Classification Search
CPC . G06T 17/00; G06T 2200/04; G06T 2210/41; A61B 34/10; A61B 34/20;
(Continued)

(56) References Cited

U.S. PATENT DOCUMENTS

| | | | |
|---|---|---|---|
| 7,609,808 B2 * | 10/2009 | Tornai | ..................... A61B 6/502 |
| | | | 600/436 |
| 11,050,990 B2 | 6/2021 | Casas | |

(Continued)

FOREIGN PATENT DOCUMENTS

| | | | | |
|---|---|---|---|---|
| WO | WO-2018115039 A1 * | 6/2018 | ............. | A61B 6/032 |
| WO | WO-2021228703 A1 * | 11/2021 | ............. | A61B 5/721 |

OTHER PUBLICATIONS

International Search Report and Written Opinion regarding International Application No. PCT/US2023/011411, dated May 10, 2023.

*Primary Examiner* — Oneal R Mistry
*Assistant Examiner* — Jongbong Nah
(74) *Attorney, Agent, or Firm* — Mueting Raasch Group

(57) ABSTRACT

Systems and methods used to perform touchless 3D scanning of a patient's face in the prone position are disclosed. In some embodiments, the systems include a rotatable 3D scanning device to capture 3D spatial data points of the patient's face and a reference frame. 3D digital mesh models are generated from the 3D spatial data points. A patient 3D digital mesh model is registered with a patient 3D model and a reference frame digital mesh model is registered with a reference frame 3D model. The 3D scanning device can include a handheld rotatable 3D scanner member or a mechanically rotatable 3D scanner member.

17 Claims, 8 Drawing Sheets

(52) U.S. Cl.
CPC ..... *A61B 2034/105* (2016.02); *G06T 2200/04*
*(2013.01); G06T 2210/41* (2013.01)

(58) Field of Classification Search
CPC ............ A61B 2034/105; A61B 5/0035; A61B
5/0037; A61B 5/0042; A61B 6/5294;
A61B 2034/2055; A61B 2090/364; A61B
2090/3762; A61B 2576/026; A61B 5/055
See application file for complete search history.

(56) References Cited

U.S. PATENT DOCUMENTS

| | | | |
|---|---|---|---|
| 2012/0022376 A1* | 1/2012 | Amara | A61B 8/4218 |
| | | | 600/443 |
| 2013/0085510 A1* | 4/2013 | Stefanchik | A61B 34/30 |
| | | | 901/30 |
| 2015/0305828 A1 | 10/2015 | Park et al. | |
| 2017/0000675 A1* | 1/2017 | Hight | A61B 6/0407 |
| 2017/0231588 A1 | 8/2017 | Shores et al. | |
| 2018/0228550 A1* | 8/2018 | Dupont | A61B 6/5247 |
| 2018/0235714 A1* | 8/2018 | Kuo | A61B 5/706 |
| 2020/0093452 A1* | 3/2020 | Bai | A61B 6/465 |
| 2021/0056699 A1* | 2/2021 | Srimohanarajah | G16H 20/40 |

* cited by examiner

ROTATING 3D SCANNER TO ENABLE PRONE CONTACTLESS REGISTRATION

TECHNICAL FIELD

The present disclosure relates generally to systems and methods to surgically treat a patient. More specifically, the present disclosure relates to systems and methods to 3D scan a patient's face in a prone position and a reference frame using a touchless or contactless technique.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
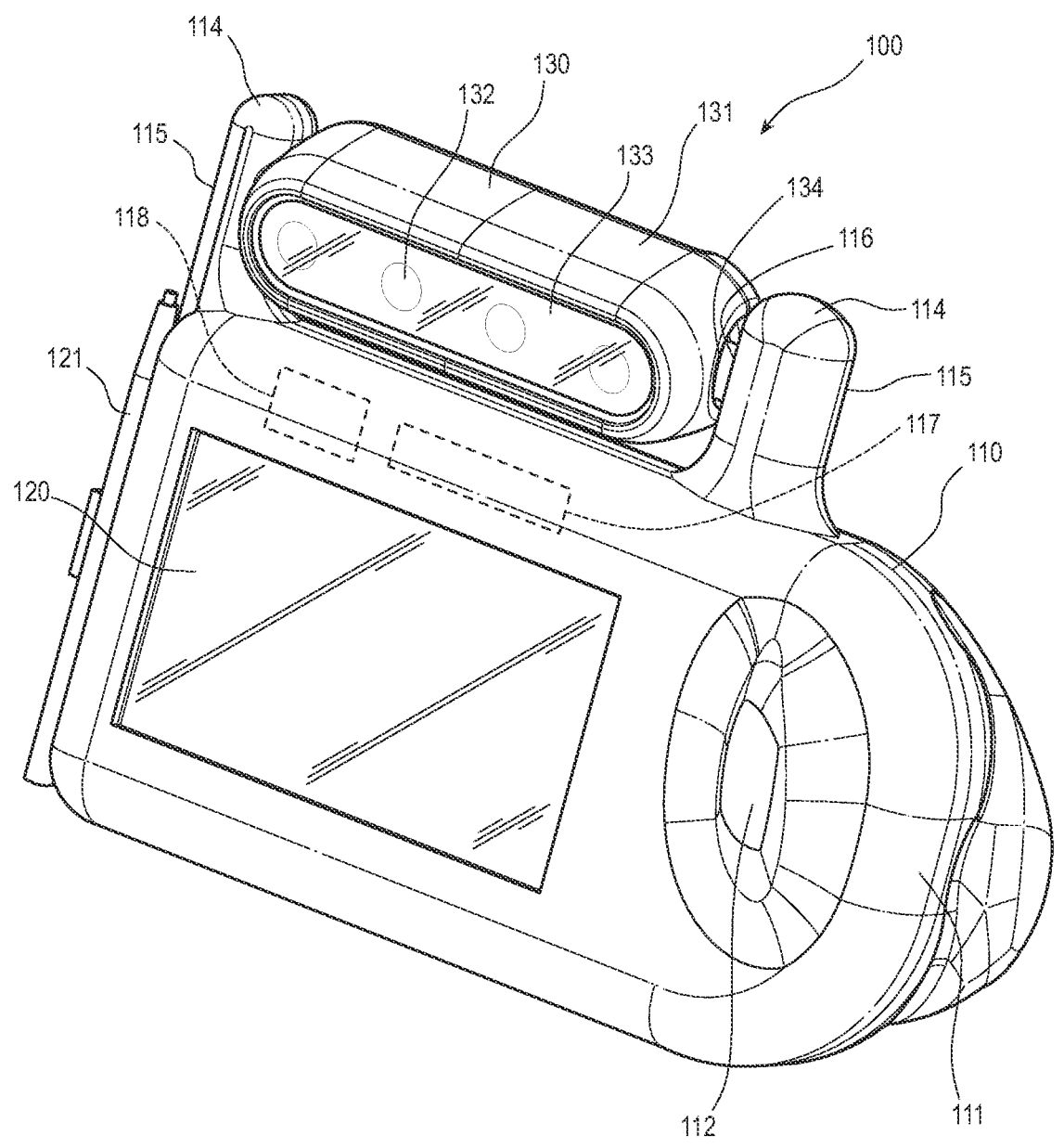
FIG. 1 is a perspective view of an embodiment of a handheld rotatable 3D scanning device.

In certain instances, a patient may require surgical treatment of an area of his/her body that is not readably accessible to a clinician, such as the patient's brain. In these instances, a medical diagnostic image of the treatment area region of interest (ROI) (e.g., patient's face) can be acquired prior to the surgical treatment. For example, the medical diagnostic image may be a magnetic resonance image (MRI) or an image from a computed tomography (CT) scan, among other images. Following positioning of the patient on a surgical table in a prone position (i.e., face down) and prior to initiation of the surgical treatment, the patient's face can be scanned with a 3D scanning device and a 3D digital mesh model of the patient's face may be generated. The 3D digital mesh model and the medical diagnostic image can be registered to provide an aligned field for electromagnetic (EM) or optical navigation during the surgical treatment.

Devices and methods within the scope of this disclosure relate to contactless or touchless registration of a digital mesh model of the patient's face and a reference frame with a medical diagnostic image to treat various regions of the body, including treatments within the brain, using EM or optical surgical navigation. Systems and methods within the scope of this disclosure include touchless scanning of the patient's face in the prone position and a reference frame by a digital imaging device having a 3D sensor of a 3D scanner member to collect spatial data points that are used to form the digital mesh model of the patient's face and the reference frame with the medical diagnostic image of the patient. Though specific examples relating to treatment of the brain are described herein, that disclosure can be analogously applied to treatment of other locations, such as the ear, nose, and throat; thoracic cavity; abdomen; and other areas.

In some embodiments within the scope of this disclosure, a handheld rotatable 3D scanning device can include a housing, a 3D scanner member, a viewing screen, a memory, and a processor. The 3D scanner member can be rotatably coupled to the housing and configured to be rotated in a direction opposite of a direction the viewing screen faces and in a direction the viewing screen faces. In an embodiment, the housing includes support members to rotatably couple the 3D scanner member to the housing. In another embodiment, the housing includes a spherical member to rotatably couple the 3D scanner member to the housing. In some embodiments, the housing may include a handle portion for grasping by the clinician.

In use, the handle of the rotatable 3D scanning device may be held by a clinician. The 3D scanner member can be rotated relative to the housing such that a camera of the 3D scanner member is oriented in the same direction the screen is facing. The 3D scanning device can be moved beneath the patient's face in a random pattern to scan the patient's face while the camera collects spatial data points. The clinician can stand to watch the screen while scanning to ensure adequate scanning of the patient's face is accomplished. The spatial data points are received by the processor to create a digital 3D mesh model of the patient's face. The digital 3D mesh model of the patient's face may be registered with a medical diagnostic image. In some embodiments, a similar method may be followed for touchless or contactless scanning of a reference frame disposed adjacent the patient's face. A digital 3D mesh model of the reference frame may be registered with a registration model of the reference frame.

In another embodiment within the scope of this disclosure, the rotatable 3D scanning device can be coupled to a patient bed. The 3D scanning device can include a motor driven scanner arm coupled to the 3D scanner and a computer coupled to the motor to control automatic 3D scanning of the patient's face in a prone position. The 3D scanner member may be coupled to the scanner arm to position the 3D scanner member underneath the patient's face. The scanner arm may rotate around a pivot point to move the 3D scanner member from a superior position to an inferior position while scanning the patient's face.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in the drawings, the drawings are not necessarily drawn to scale unless specifically indicated.

Figure 2:
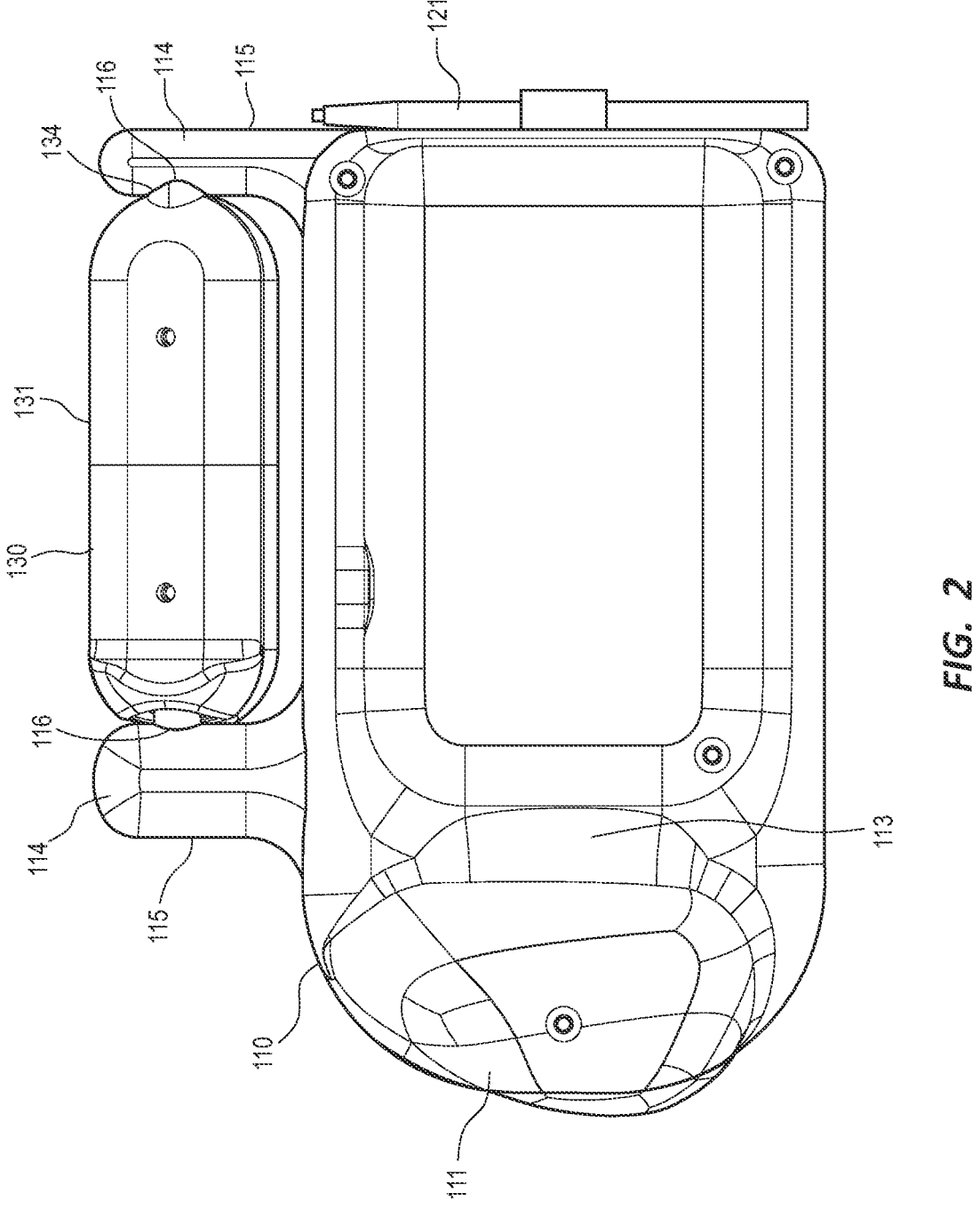
FIG. 2 is a back view of the handheld rotatable 3D scanning device of FIG. 1.
Figure 3:
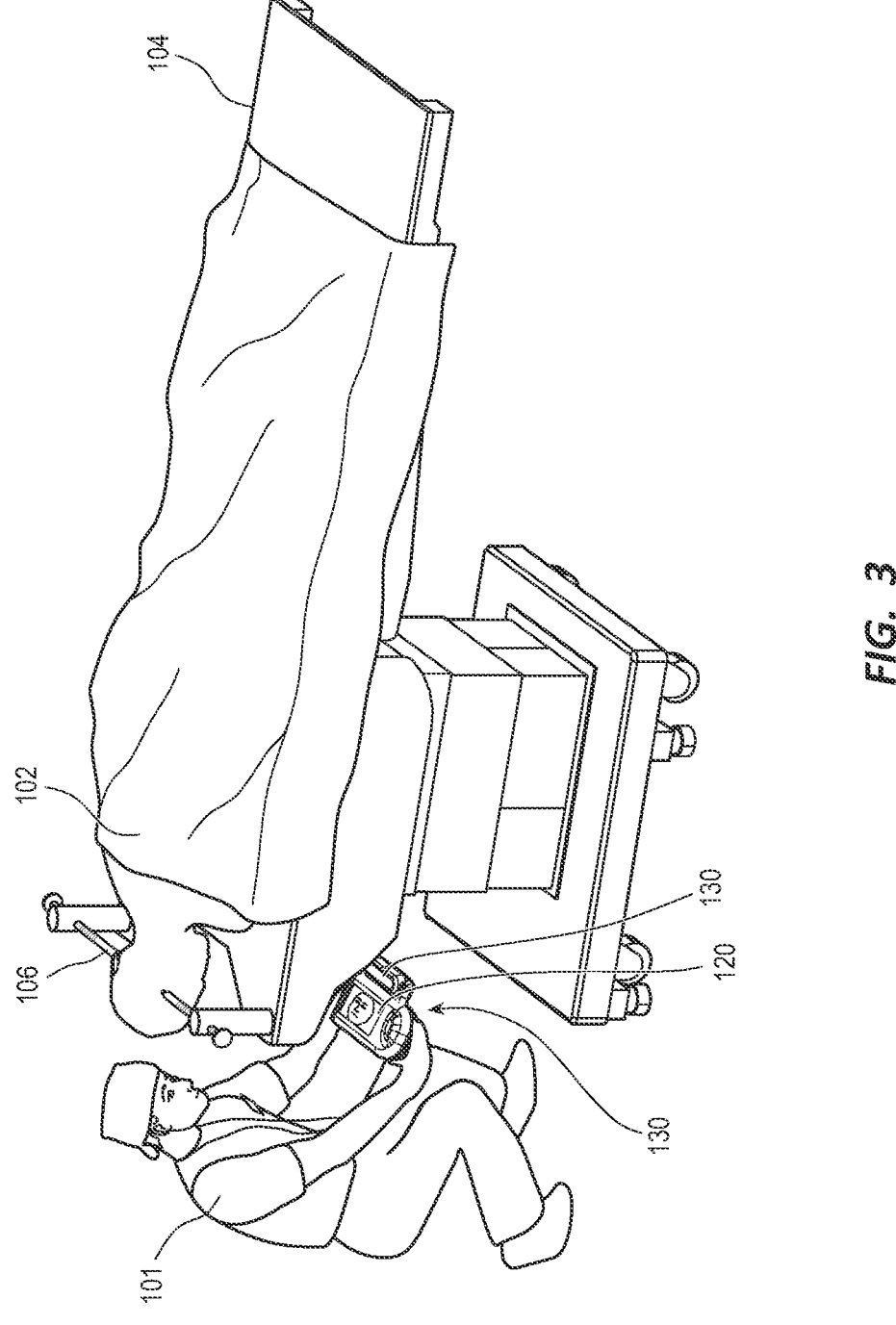
FIG. 3 is a perspective view of a method of 3D scanning a patient's face in the prone position using the handheld 3D scanning device of FIG. 1.
Figure 5:
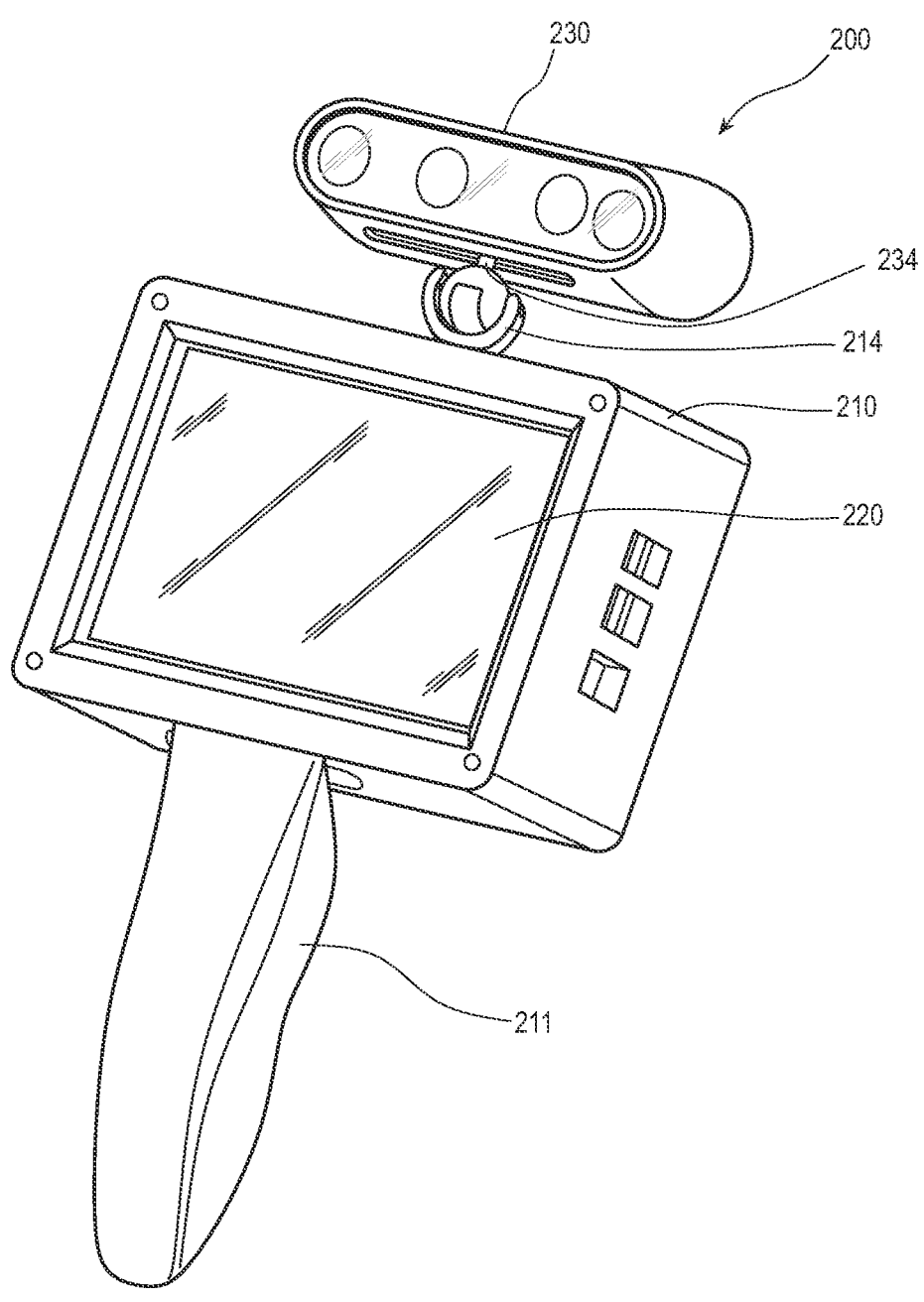
FIG. 5 is perspective view of another embodiment of a handheld rotatable 3D scanning device.
Figure 6:
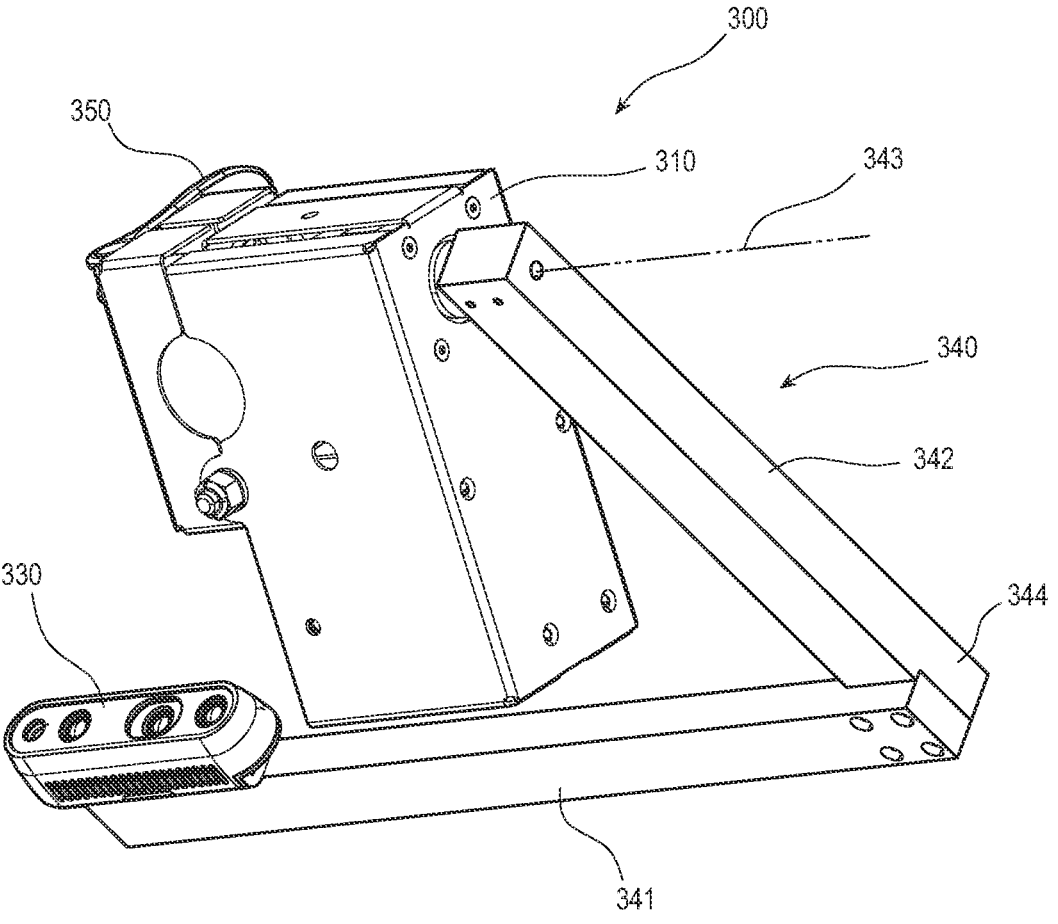
FIG. 6 is a front perspective view of an embodiment of a mechanical rotatable 3D scanning device.
Figure 7:
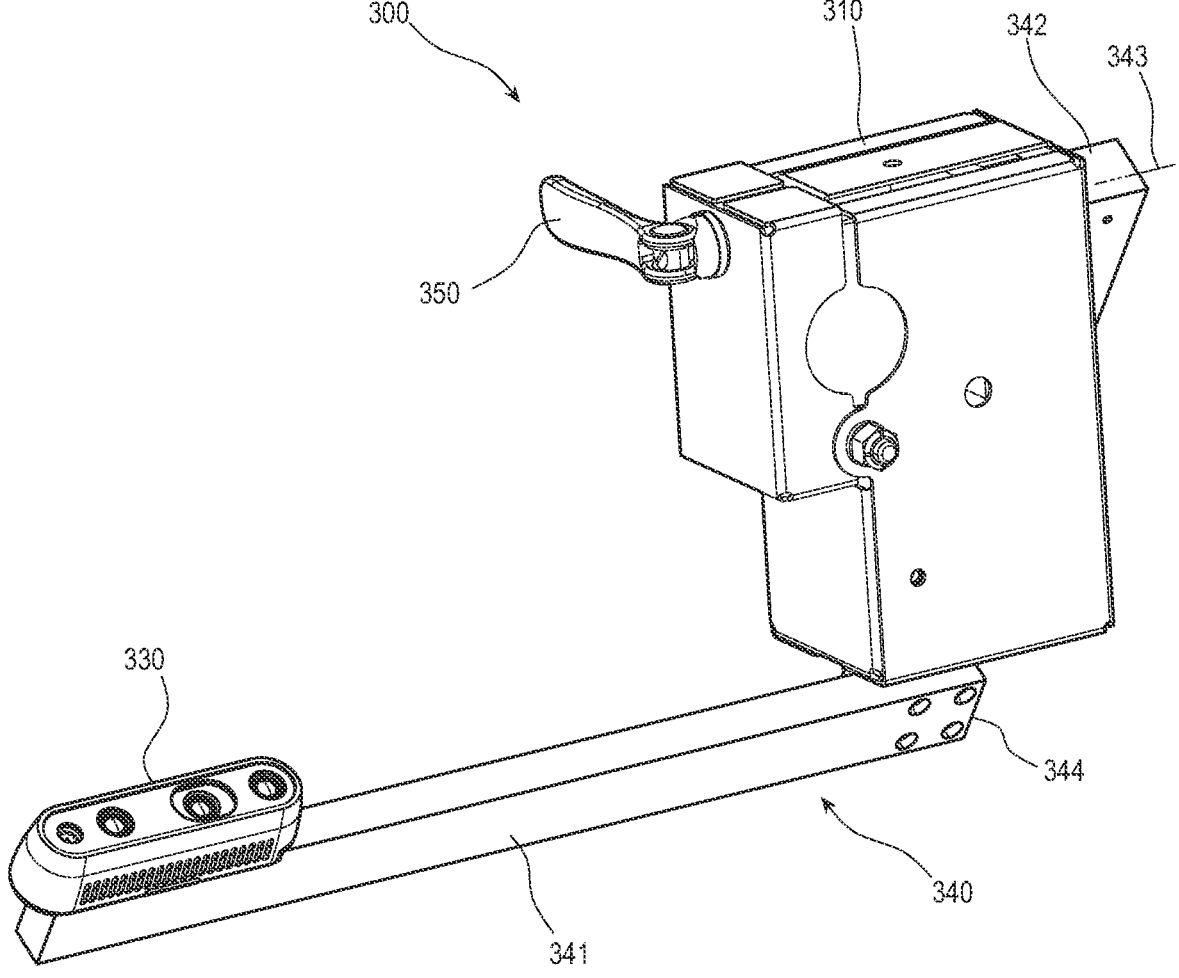
FIG. 7 is a back perspective view of the mechanical rotatable 3D scanning device of FIG. 6.
Figure 8:
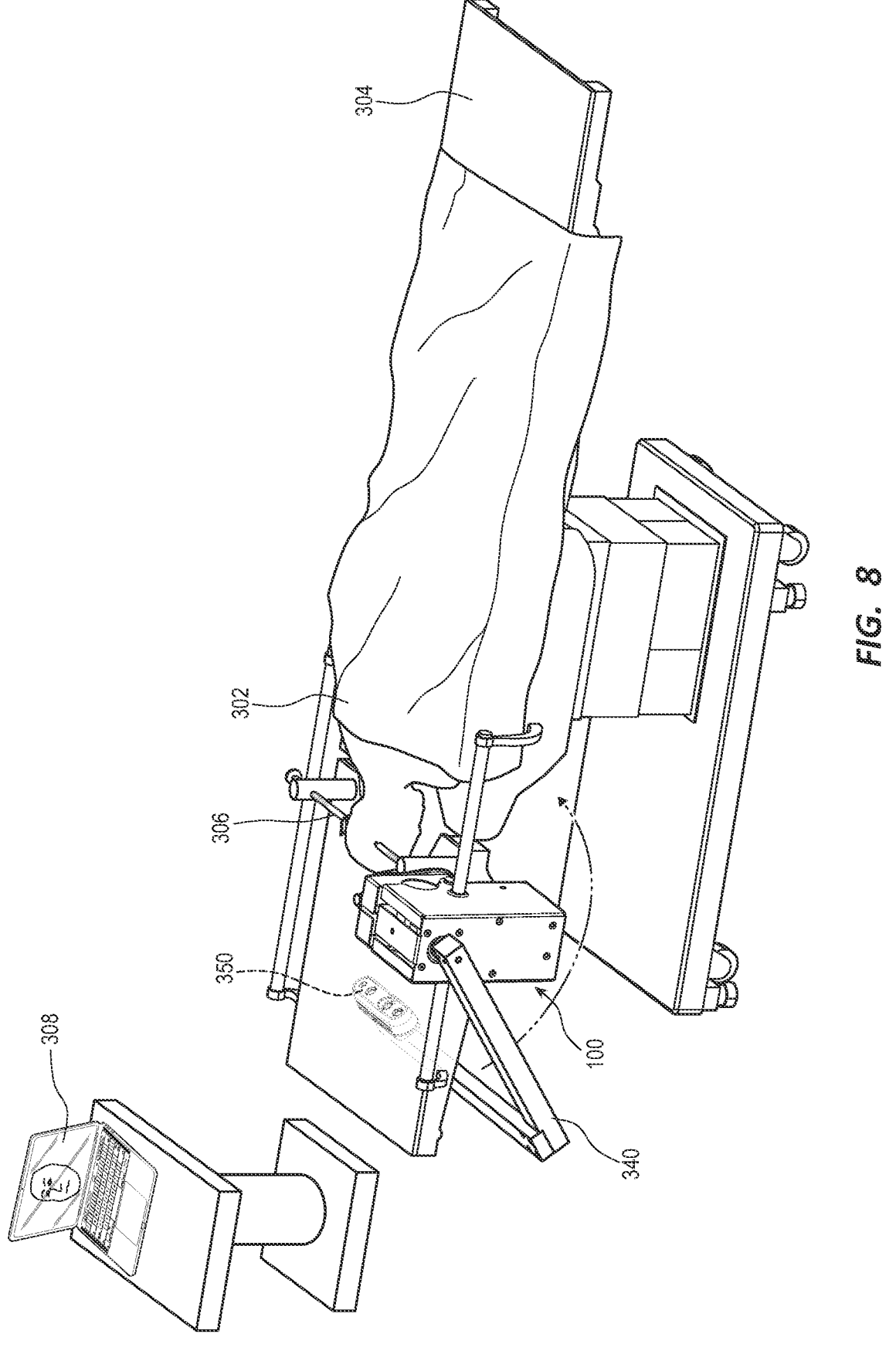
FIG. 8 is perspective view of a method of 3D scanning the patient's face in the prone position using the mechanical rotatable scanning device of FIG. 6.

FIGS. 1-3 illustrate an embodiment of a handheld rotatable 3D scanning device. FIG. 5 illustrates another embodiment of a handheld rotatable 3D scanning device. FIGS. 6-8 illustrate an embodiment of a mechanical rotatable 3D scanning device. Further, in some views only selected components are illustrated to provide detail into the relationships of the components. Some components may be shown in multiple views, but not discussed in connection with every view. Disclosure provided in connection with any figure is relevant and applicable to disclosure provided in connection with any other figure or embodiment.

FIGS. 1 and 2 illustrate an embodiment of a handheld 3D scanning device 100. As depicted, the handheld 3D scanning device 100 includes a housing 110, an electronic memory 117, a processor 118, a viewing screen or display 120, and a rotatable 3D scanner member 130. The housing 110 is generally rectangularly shaped. In other embodiments, the housing 110 may include any suitable shape, such as square, circular, elliptical, etc. The housing 110 includes a handle portion 111 having a thumb grip 112 disposed on a front side of the housing 110 and a finger grip 113 (shown in FIG. 2) disposed on a back side of the housing 110. The handle portion 111 can be configured to enable the clinician to grasp the handle portion 111 such that the viewing screen 120 is facing toward the clinician as the patient's face is scanned by the 3D scanner member 130.

The housing 110 includes support members 114 extending from a top side of the housing 110. Each of the depicted support members 114, includes a post 115 and a recess 116 sized to rotatably couple to a pivot arm 134 of the rotatable 3D scanner member 130. The rotatable 3D scanner member 130 includes a scanner housing 131. A digital imaging device 132 is disposed within the scanner housing 131. The digital imaging device 132 may include a laser imaging detection and ranging (LiDAR) sensor configured to scan 3D contours of the patient's face and a memory to collect spatial data points. In some embodiments, the digital imaging device 132 may be covered by a lens 133 configured to focus reflected laser light to the LiDAR chip and to protect the LIDAR chip.

The scanner housing 131 also includes a pivot arm 134 extending from each end of the scanner housing 131. The pivot arms 134 are sized to be received by and rotate within the recesses 116 of the support members 114. The pivot arms 134 may rotate from about zero degrees to about 360 degrees and may rotate about 180 degrees. In some embodiments, the recesses 116 may include detents configured to engage with recesses of the pivot arms 134. The detents and recesses may be configured to provide a rotation resistance when the rotatable 3D scanner member 130 is rotated from a first position facing in a direction the viewing screen 120 faces, as shown in FIG. 1, to a second position facing away from the direction the viewing screen 120 is facing, as shown in FIG. 2. In some embodiments, the detents and recesses may be circumferentially spaced about 180 degrees apart. In other embodiments, the detents and recesses may be circumferentially spaced about 90 degrees apart.

In some embodiments, an electronic cable is magnetically coupled to the rotatable 3D scanner member 130 and routed through the support member 114 into the housing 110 and coupled to the electronic memory 117 and processor 118. The electronic cable can facilitate communication between the rotatable 3D scanner member 130 and the electronic memory 117 and/or the processor 118 when the rotatable 3D scanner member 130 is rotated.

The processor 118 may be used to process executable code and data stored in the electronic memory 117. The electronic memory 117 may include static RAM, dynamic RAM, flash memory, one or more flip-flops, or other electronic storage medium. The electronic memory 117 may include a plurality of engines or modules and data. The engines may run multiple operations serially, concurrently or in parallel on the processors 118.

The viewing screen 120 may be any suitable type of screen enabling the clinician to view real time collection of special data points of the patient's face and to view a 3D mesh model of the patient's face. For example, the viewing screen 120 may be a touch screen. A stylus 121 may be used to interface with the viewing screen 120 to provide user input to the memory and a processor of the 3D scanning device 100.

FIG. 3 illustrates a method of touchless or contactless scanning of a patient's face in the prone position using the 3D scanning device 100. As illustrated, a patient 102 is positioned on a surgical table 104 in the prone position, such that the face of the patient 102 is facing downward, toward the floor. In other embodiments, the patient 102 may be positioned in a supine or lateral position. The patient's head can be held in place by a head clamp 106 (e.g., a Mayfield head clamp). A clinician 101 may stand adjacent the patient's head and hold the 3D scanning device 100 in one or two hands beneath the face of the patient 102. The viewing screen 120 and the rotatable 3D scanner member 130 are oriented such that the viewing screen 120 and the 3D scanner member 130 are facing the face of the patient 102. In this orientation, the clinician 101 can stand and view the viewing screen 120 while moving the 3D scanning device 100 around the face of the patient 102 to collect spatial data points of the face of the patient 102. In other embodiments, when the patient 102 is in the supine or lateral positions, the 3D scanner member 130 can be rotated to face away from the viewing screen 120 and toward the patient 102.

Figure 4:
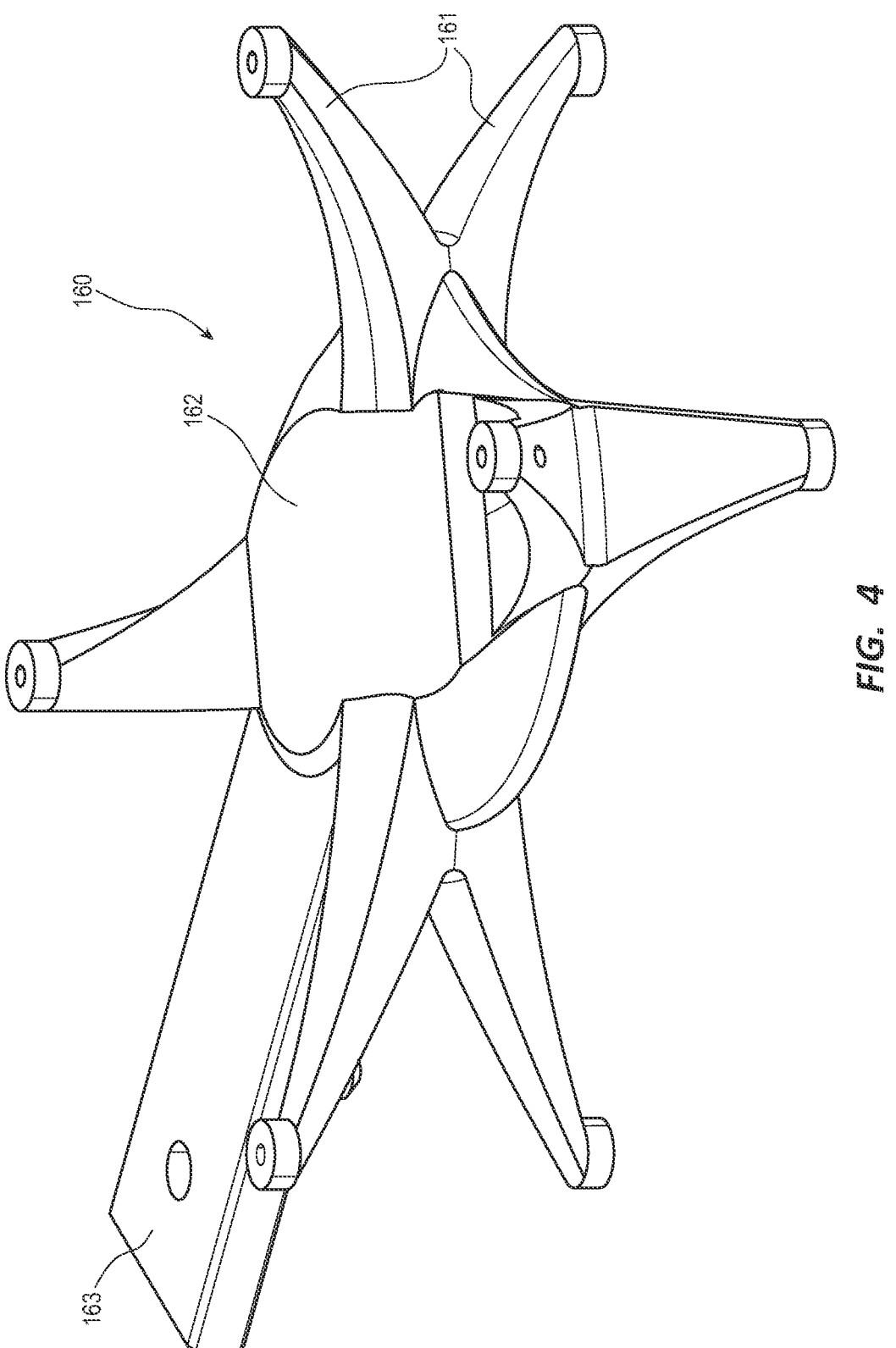
FIG. 4 is a perspective view of an embodiment of a reference frame.

In some embodiments, the 3D scanning device can simultaneously scan a reference frame 160 disposed adjacent the patient's head and collect spatial data points of the reference frame 160. As illustrated in FIG. 4, the reference frame 160 may be double-sided and include 3D identifiable arms 161 extending radially outward from a central portion 162. The number of arms 151 may be one, two, three, four, or more. In another embodiment, the reference frame 161 may include other 3D identifiable features, such as spheres, polygonal shaped objects, etc. coupled to the ends of the arms 151. The reference frame 160 may also include mirrors coupled to either side or both sides. An attachment bar 163 may extend from the central portion 162 and be configured to couple the reference frame 160 to the surgical table 104 adjacent the patient's head.

When 3D scanning of the patient's face and the reference frame is completed, the processor of the 3D scanner member 130 utilizes the spatial data points of the patient's face to form a patient digital 3D mesh model and the spatial data points of the reference frame to form a reference frame digital 3D mesh model. The patient digital 3D mesh model may be registered with a 3D patient registration model from a 3D diagnostic image (e.g., CT image, MRI, computer tomography angiography (CTA) image, magnetic resonance angiography (MRA) image, and intraoperative CT image) and the reference frame digital 3D mesh model may be registered with a reference frame digital 3D model.

FIG. 5 depicts an embodiment of a handheld 3D scanning device 200 that resembles the 3D scanning device 100 described above in certain respects. Accordingly, like features are designated with like reference numerals, with the leading digit incremented to "2." For example, the embodiment depicted in FIG. 5 includes a 3D scanner member 230 that may, in some respects, resemble the 3D scanner member 130 of FIG. 1. Relevant disclosure set forth above regarding similarly identified features thus may not be repeated hereafter. Moreover, specific features of the 3D scanning device 100 and related components shown in FIGS. 1-3 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the 3D scanning device 200 and related components depicted in FIG. 5. Any suitable combination of the features, and variations of the same, described with respect to the 3D scanning device 100 and related components illustrated in FIGS. 1-3 can be employed with the 3D scanning device 200 and related components of FIG. 5, and vice versa. This pattern of disclosure applies equally to further embodiments depicted in subsequent figures and described hereafter, wherein the leading digits may be further incremented.

As illustrated in FIG. 5, the 3D scanning device 200 includes a housing 210, a viewing screen 220, and a rotatable 3D scanner member 230. The housing 210 includes a handle 211 extending from a bottom side of the housing 210. The handle 211 can be sized and include grip features to facilitate grasping of the handle 211 by the clinician's hand.

The housing 210 includes a spherical socket member 214 extending from a top side of the housing 210. The spherical socket member 214 is configured to receive a spherical member 234 of the 3D scanner member 230. When coupled together, the spherical socket member 214 and the spherical member 234 allow the 3D scanner member 230 to be rotated from about zero degrees to about 360 degrees about a vertical axis of the 3D scanner member 230 such that the 3D scanner member 230 can be oriented to face the direction the viewing screen 220 faces and to face a direction away from the direction the viewing screen 220 faces.

FIGS. 6-8 illustrate an embodiment of a mechanical 3D scanning device 300. As depicted in FIGS. 6 and 7, the 3D scanning device 300 includes a drive housing 310, a scanner arm 340, and a 3D scanner member 330. The drive housing 310 includes a motor and a transmission (e.g., a gearbox) disposed within the drive housing 310 and coupled to the scanner arm 340. The scanner arm 340 includes a horizontal portion 341 and a vertical portion 342. The horizontal portion 341 can be coupled to the vertical portion 342 at a joint 344 having a joint angle that may be about 90 degrees. In certain embodiments, the joint 344 may be adjustable. In some embodiments, the scanner arm 340 may include 1, 2, 3, or more joints. In other embodiments the scanner arm 340 can include a unibody construct. The 3D scanner member 330 is coupled to the horizontal portion 341 of the scanner arm 340 and oriented to face upward. The motor and transmission are configured to drive rotation of the scanner arm 340 about a rotation axis 343 adjacent an end of the vertical portion 342 of the scanner arm 340. Rotation of the scanner arm 340 may cause the horizontal portion 341 and the 3D scanner member 330 to be rotated forward and backward in an arc measure of up to about 120 degrees under the patient's face.

The 3D scanning device 300 can further include a clamp member 350 coupled to the housing 310 and configured to attach the 3D scanning device 300 to a surgical table adjacent a patient's head. The clamp member 350 can be of any suitable type to securely attach the housing 310 to the surgical table. When clamped to the surgical table, the 3D scanner member 330 is positioned below the patient's face when the patient is in the prone position.

The motor of the 3D scanning device 300 may be activated by actuation of a switch (e.g., a button) by the clinician. In another embodiment, the motor can be coupled to a computer configured to control the motor. The computer may communicate with the motor via a wired connection or via a wireless connection. The clinician may provide input to the computer to control the function of the motor.

FIG. 8 illustrates a method of touchless or contactless scanning of a patient's face in the prone position using the 3D scanning device 300. As illustrated, a patient 302 is positioned on a surgical table 304 in the prone position, such that the face of the patient 302 is facing downward, toward the floor. In other embodiments, the patient 302 may be positioned in a supine or lateral position. The head of the patient 302 can be held in place by a head clamp 306 (e.g., a Mayfield head clamp). The 3D scanning device 300 is attached to the surgical table 304 adjacent the head of the patient 302 such that the 3D scanner member 330 is positioned below the face of the patient 302. The motor of the 3D scanning device 300 may be activated by the clinician by actuating a switch or remotely by use of a computer 308 to activate the motor. When the motor is activated, the scanner arm 340 is rotated longitudinally back and forth, as indicated by the arrow of FIG. 8, allowing the 3D scanner member 330 to scan the face of the patient 302 from a superior position to an inferior position relative to the patent's face. As the 3D scanner member 330 scans the face of the patient 302, the 3D scanner member 330 collects spatial data points of the face of the patient 302.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of touchless registration, comprising optically scanning a region of interest (ROI) of a patient and a reference frame using an optical scanning device to capture a collection of optical data points; constructing an ROI digital mesh model from the collection of optical data points; detecting an anatomical feature of the ROI digital mesh model and a corresponding anatomical feature of a patient registration model utilizing a facial detection algorithm; weighting the anatomical feature of the ROI digital mesh model and the corresponding anatomical feature of the patient registration model; and registering the ROI digital mesh model with the patient registration model utilizing the weighted anatomical features of the ROI digital mesh model and the patient registration model to generate a navigation space. Other steps are also contemplated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

References to approximations are made throughout this specification, such as by use of the term "about." For each such reference, it is to be understood that, in some embodiments, the value, feature, or characteristic may be specified without approximation. For example, where the qualifier "about" is used, this term includes within its scope the qualified word in the absence of its qualifiers.

The terms "a" and "an" can be described as one, but not limited to one. For example, although the disclosure may recite a generator having "an electrode," the disclosure also contemplates that the generator can have two or more electrodes.

Unless otherwise stated, all ranges include both endpoints and all numbers between the endpoints.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method of touchless registration for a surgical procedure, comprising:
positioning a patient on the surgical bed in a prone position;
positioning a hand-held housing of a scanning device held by a user relative to the patient, the hand-held housing including a first support member and a second support member extending from a top side of the hand-held housing, the first and second support members each including a post and a recess, each recess including a plurality of detents;

rotating relative to the hand-held housing of the scanning device a rotatable 3D scanner member that is rotatably coupled to and carried by the hand-held housing of the scanning device,
wherein the rotatable 3D scanner member comprises a scanner housing that includes a first end and a second end, the first end including a first pivot arm extending from the scanner housing towards the first support member of the hand-held housing and configured to engage with the detents of the recess of the first support member, the second end including a second pivot arm extending from the scanner housing towards the second support member of the hand-held housing and configured to engage with the detents of the recess of the second support member, and
wherein the rotatable 3D scanner member includes an imaging device that is directed toward the patient's face as the patient is in the prone position on the surgical bed and the hand-held housing is held by the user;
moving the rotatable 3D scanner member relative to the patient's face to capture a first collection of spatial data points with the imaging device of the rotatable 3D scanner member;
constructing a first digital mesh model of the patient's face from the first collection of spatial data points; and
registering the first digital mesh model with a patient registration model.

2. The method of claim 1, wherein moving the 3D scanner member relative to the patient's face comprises moving the 3D scanner member in a random pattern as the patient is in the prone position on the surgical bed.

3. The method of claim 1, wherein moving the 3D scanner member relative to the patient's face comprises moving the 3D scanner member from a superior portion of the patient's face to an inferior portion of the patient's face in a single plane as the patient is in the prone position on the surgical bed.

4. The method of claim 1, wherein one or more of the steps of moving the 3D scanner member relative to the patient's face; constructing a first digital mesh model of the patient's face; and registering the first digital mesh model of the patient's face with a patient registration model are accomplished automatically.

5. The method of claim 1, wherein the scanning device further comprises:
a memory to receive the first collection of spatial data points from the 3D scanner member;
a processor to construct the first digital mesh model from the first collection of spatial data points; and
a viewing screen coupled to the housing, wherein the 3D scanner member is rotatable relative to the viewing screen.

6. The method of claim 5, further comprising rotating the 3D scanner member relative to the handheld housing to face in a direction opposite of a direction the viewing screen faces.

7. The method of claim 5, further comprising rotating the 3D scanner member relative to the handheld housing to face in a same direction the viewing screen faces as the patient is in the prone position on the surgical bed.

8. The method of claim 1, wherein the 3D scanner member comprises a digital imaging sensor comprising a laser imaging detection and ranging sensor.

9. The method of claim 1, further comprising creating the patient registration model from any one of a computed tomography (CT) image, magnetic resonance image (MRI), computer tomography angiography (CTA) image, magnetic resonance angiography (MRA) image, and intraoperative CT image.

10. The method of claim 1, further comprising disposing a reference frame adjacent the patient's face.

11. The method of claim 10, further comprising:

rotating the 3D scanner member toward the reference frame; moving the 3D scanner member around the reference frame;

scanning the reference frame using the 3D scanner member to capture a second collection of spatial data points;

constructing a second digital 3D mesh model of the reference frame from the second collection of spatial data points; and registering the second digital mesh model with a reference frame 3D model.

12. A rotatable scanning device, comprising:

a drive housing;

a clamp attached to the drive housing to selectively fix the drive housing and the rotatable scanning device to a surgical table adjacent to a patient's head when the patient is lying in a prone position on the surgical table;

a 3D scanner member comprising a digital imaging sensor configured to capture spatial data points;

a rotatable scanner arm coupled to the 3D scanner member and the drive housing and configured to move the 3D scanner member relative to the patient's face; and a rotational drive mechanism housed in the drive housing and operably coupled to the rotatable scanner arm and configured to drive rotational movement of the rotatable scanner arm around a pivot point to cause the scanner to arm rotate longitudinally along a length of the surgical table.

13. The rotatable scanning device of claim 12, further comprising a computer coupled to the rotational drive mechanism and the 3D scanner member and configured to automatically control operation of the rotational drive mechanism and receipt of the spatial data points from the 3D scanner member.

14. The rotatable scanning device of claim 12, wherein the rotational drive mechanism comprises:

a motor; and a transmission configured to drive movement of the rotatable scanner arm.

15. The rotatable scanning device of claim 12, wherein the rotatable scanner arm includes a first arm coupled to a second arm and configured to move the 3D scanner in a single vertical plane.

16. The rotatable scanning device of claim 12, wherein the digital imaging sensor comprises a laser imaging detection and ranging sensor.

17. A handheld rotatable scanning device, comprising:

a device housing configured to be held by a user, the housing comprising a first support member and a second support member extending from a top side of the housing, the first and second support members each including a post and a recess, each recess including a plurality of detents;

a rotatable 3D scanner member rotatably coupled to and carried by the housing and configured to rotate relative to the device housing, the rotatable 3D scanner member comprising a scanner housing that includes a first end and a second end, the first end including a first pivot arm extending from the scanner housing towards the first support member of the device housing and configured to engage with the detents of the recess of the first support member, the second end including a second pivot arm extending from the scanner housing towards the second support member of the device housing and configured to engage with the detents of the recess of the second support member, the rotatable 3D scanner member having a rotatable digital imaging sensor configured to capture a collection of spatial data points;

a memory to receive the collection of spatial data points from the rotatable digital imaging sensor;

a processor to construct a digital mesh from the collection of spatial data points; and a display coupled to the housing, wherein the rotatable 3D scanner member is rotatable relative to the housing and the display, wherein the rotatable 3D scanner member is rotatable from a first orientation where the rotatable 3D scanner member and the display face a patient and a second orientation where the rotatable 3D scanner member faces away from the display while facing toward the patient.

* * * * *